(12) United States Patent
Kubo et al.

(10) Patent No.: US 8,825,143 B2
(45) Date of Patent: *Sep. 2, 2014

(54) MEDICAL APPARATUS FOR CONTROL OF EXCITATION LIGHT BASED ON IMAGE SENSOR POSITION AND FLUORESCENT DRUG INFORMATION

(75) Inventors: Kei Kubo, Hino (JP); Hideyuki Kugimiya, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/617,718

(22) Filed: Sep. 14, 2012

(65) Prior Publication Data

US 2013/0012815 A1  Jan. 10, 2013

Related U.S. Application Data

(63) Continuation of application No. PCT/JP2011/079015, filed on Dec. 15, 2011.

(30) Foreign Application Priority Data

Mar. 15, 2011  (JP) .................................. 2011-056878

(51) Int. Cl.
| | |
|---|---|
| *A61B 6/00* | (2006.01) |
| *A61B 5/00* | (2006.01) |
| *A61B 1/04* | (2006.01) |
| *A61B 1/045* | (2006.01) |
| *A61B 1/00* | (2006.01) |

(52) U.S. Cl.
CPC .............. *A61B 1/041* (2013.01); *A61B 5/0059* (2013.01); *A61B 1/045* (2013.01); *A61B 5/0071* (2013.01); *A61B 1/00147* (2013.01); *A61B 1/043* (2013.01); *A61B 5/0086* (2013.01)
USPC ........................... 600/477; 600/109; 600/160

(58) Field of Classification Search
None
See application file for complete search history.

(56) References Cited

U.S. PATENT DOCUMENTS 6,428,469 B1 *  8/2002  Iddan et al. ................... 600/109
6,635,834 B1 * 10/2003  Wenner ....................... 200/61.08

(Continued)

FOREIGN PATENT DOCUMENTS

| CN | 101573068 A | 11/2009 |
|---|---|---|
| JP | 04-176443 | 6/1992 |

(Continued)

*Primary Examiner* — Unsu Jung
*Assistant Examiner* — Amanda Lauritzen Moher
(74) *Attorney, Agent, or Firm* — Scully, Scott, Murphy & Presser, P.C.

(57) ABSTRACT

A medical apparatus includes a storing section in which information concerning a drug movement in a living body is stored for each of types of a plurality of fluorescent drugs, an arithmetic processing section that acquires, based on the information stored in the storing section, information concerning a target region to which a fluorescent drug is administered, information concerning a method of administering the fluorescent drug to the target region, and information indicating start of administration of the fluorescent drug, information concerning diagnosis start timing, an image pickup section, a position information acquiring section that acquires position information of the image pickup section, and a light source control section that stops, at least from the administration start timing to the diagnosis start timing, irradiation of excitation light and irradiates the excitation light based on the diagnosis start timing and the position information.

3 Claims, 9 Drawing Sheets

(56) References Cited

U.S. PATENT DOCUMENTS

| | | | |
|---|---|---|---|
| 6,709,387 B1 * | 3/2004 | Glukhovsky et al. | 600/109 |
| 8,216,130 B2 * | 7/2012 | Glukhovsky et al. | 600/118 |
| 2001/0051766 A1 * | 12/2001 | Gazdzinski | 600/309 |
| 2004/0111011 A1 | 6/2004 | Uchiyama et al. | |
| 2004/0260150 A1 * | 12/2004 | Bernstein | 600/139 |
| 2005/0226815 A1 | 10/2005 | Kawakami et al. | |
| 2005/0288594 A1 * | 12/2005 | Lewkowicz et al. | 600/478 |
| 2006/0089554 A1 | 4/2006 | Ishihara et al. | |
| 2006/0188402 A1 * | 8/2006 | Xie et al. | 422/82.08 |
| 2008/0161643 A1 | 7/2008 | Uchiyama et al. | |

FOREIGN PATENT DOCUMENTS

| | | |
|---|---|---|
| JP | 2003-261464 | 9/2003 |
| JP | 2004-041709 | 2/2004 |
| JP | 2006-061683 | 3/2006 |
| JP | 2006-122131 | 5/2006 |
| JP | 2007-175188 | 7/2007 |
| JP | 2007-303990 | 11/2007 |
| WO | WO 03/074091 A2 | 9/2003 |

* cited by examiner

FIG.7
FLUORESCENT DRUG A
| ADMINISTERING METHOD \ TARGET REGION | LARGE INTESTINE | STOMACH | ESOPHAGUS | ... |
|---|---|---|---|---|
| INTRAVENOUS INJECTION | DRUG MOVEMENT A01 | DRUG MOVEMENT A02 | DRUG MOVEMENT A03 | ... |
| SPRAYING | DRUG MOVEMENT A11 | DRUG MOVEMENT A12 | DRUG MOVEMENT A13 | ... |
| ⋮ | ⋮ | ⋮ | ⋮ | |
FIG.8
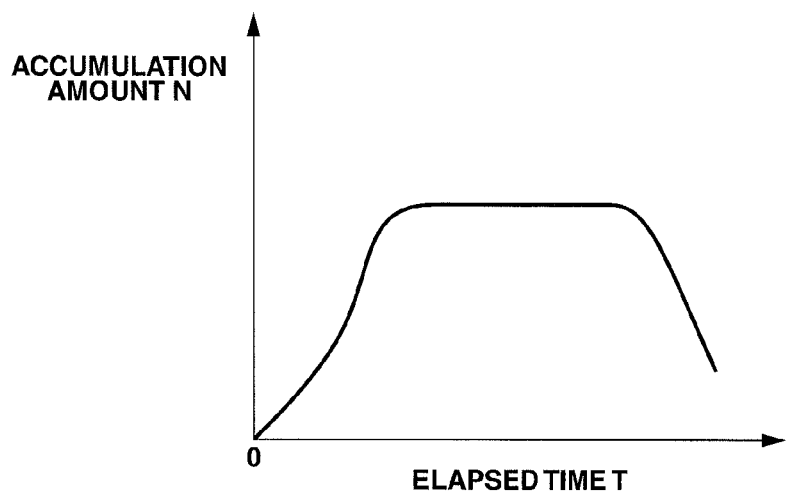
FIG.9
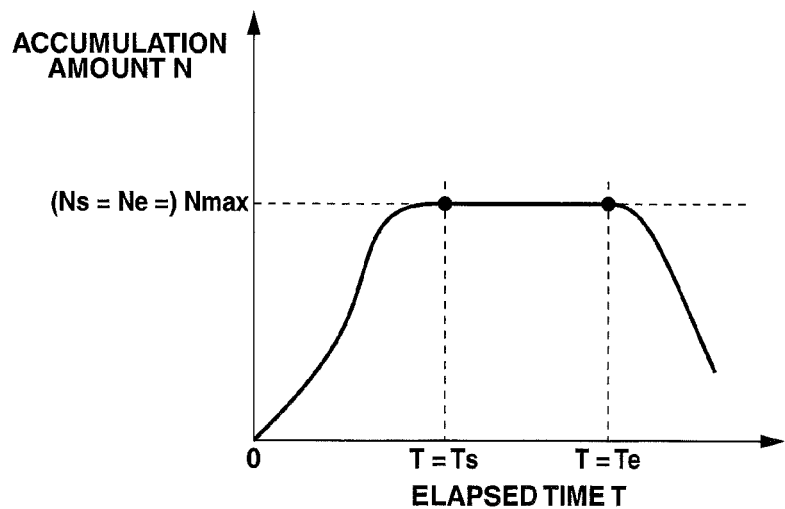

MEDICAL APPARATUS FOR CONTROL OF EXCITATION LIGHT BASED ON IMAGE SENSOR POSITION AND FLUORESCENT DRUG INFORMATION

CROSS REFERENCE TO RELATED APPLICATION

This application is a continuation application of PCT/JP2011/079015 filed on Dec. 15, 2011 and claims benefit of Japanese Application No. 2011-056878 filed in Japan on Mar. 15, 2011, the entire contents of which are incorporated herein by this reference.

BACKGROUND OF THE INVENTION

1. Field of the Invention

The present invention relates to a medial apparatus and, more particularly, to a medical apparatus capable of performing observation based on fluorescence emitted from a fluorescent drug.

2. Description of the Related Art

In recent years, a cancer diagnosis technique employing a molecular target drug has started to attract attention. Specifically, for example, a method of, after administering a fluorescent drug (a fluorescent probe) targeting living body protein, which specifically develops in a cancer cell, to a living body, determining presence or absence of cancer based on fluorescence emitted in a target region of the living body has been studied in recent years. Such a method is useful in early detection of cancer in a digestive tract field.

As an application of the method, a method of, after administering plural kinds of fluorescent drugs having different fluorescence wavelengths to a living body, complexly observing, based on plural fluorescences emitted in a target region of the living body, development states of plural kinds of living body protein corresponding to the plural kinds of fluorescent drugs is being proposed. Such a method is considered to be useful in, for example, estimation of a stage of cancer, prediction of an infiltration risk of cancer, and prediction of a metastasis risk of cancer.

For example, Japanese Patent Application Laid-Open Publication No. 2006-61683 discloses an endoscope apparatus including a laser beam source that generates excitation light, an endoscope scope including an irradiating section of the excitation light at a distal end portion thereof, an intensifier incorporating a charge coupled device (hereinafter abbreviated as CCD that detects fluorescence generated in a subject by the excitation light, fluorescent image generating means for generating a fluorescent image signal based on a fluorescent signal from the intensifier incorporating CCD, distance measuring means for generating a distance signal corresponding to a distance between the irradiating section and the subject, fluorescence amount calculating means for correcting the fluorescent signal with the distance signal and calculating a fluorescence amount not affected by fluctuation in the distance. In the endoscope apparatus, the fluorescence amount calculating means includes time-after-drug-administration correcting means for correcting the fluorescent signal or the fluorescent image signal based on an elapsed time after the fluorescent drug is administered.

The configuration disclosed in Japanese Patent Application Laid-Open Publication No. 2006-61683 makes it possible to correct, even before the influence of the administered fluorescent drug spreads all over the subject, a fluorescent image to a state after the influence of the fluorescent drug spreads all over the subject.

SUMMARY OF THE INVENTION

A medical apparatus according to an aspect of the present invention includes: a storing section in which information concerning a drug movement in a living body is stored in advance for each of types of a plurality of fluorescent drugs; an arithmetic processing section that acquires, based on the information stored in the storing section, information concerning a target region of a subject to which a desired fluorescent drug is administered, information concerning a method of administering the desired fluorescent drug to the target region, and information indicating start of administration of the desired fluorescent drug, information concerning diagnosis start timing corresponding to the desired fluorescent drug; an image pickup section that picks up an image of an object in the subject; a position information acquiring section that acquires position information of the image pickup section in the subject; and a light source control section that controls, at least from the administration start timing to the diagnosis start timing, irradiation of excitation light for exciting the desired fluorescent drug to a stopped state and controls the excitation light to an irradiatable state based on the diagnosis start timing and the position information.

BRIEF DESCRIPTION OF THE DRAWINGS

FIG. 7 is a diagram showing an example of table data used in selecting a drug movement of a fluorescent drug;

FIG. 8 is a diagram showing an example of a drug movement selected out of the table data;

FIG. 9 is a diagram showing an example of a diagnosis start time and a diagnosis end time acquired when the drug movement shown in FIG. 8 is selected;

DETAILED DESCRIPTION OF THE PREFERRED EMBODIMENT

An embodiment of the present invention is explained below with reference to the drawings.

FIGS. 1 to 13 relate to the embodiment of the prevent invention.

Figure 1:
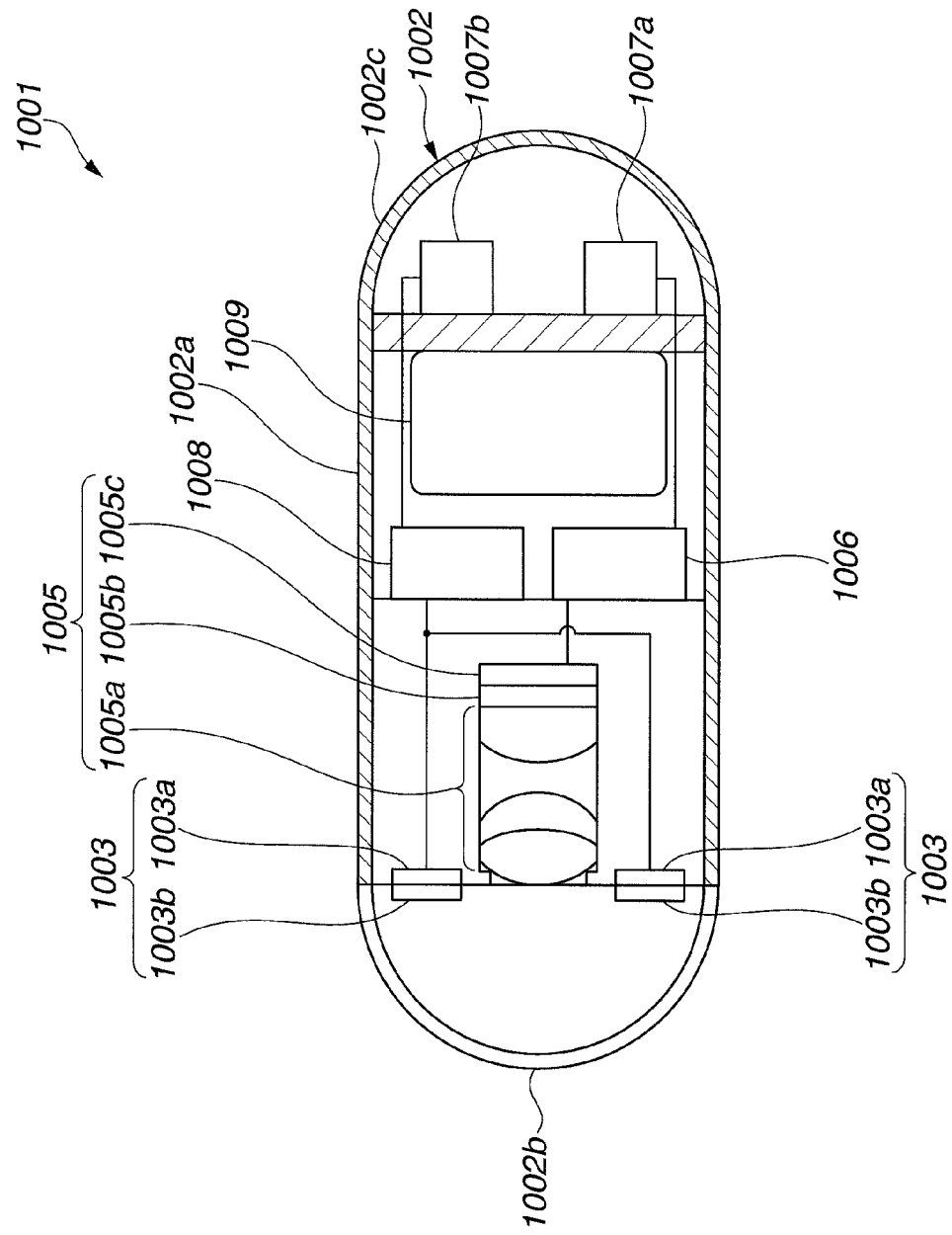
FIG. 1 is a diagram showing a configuration of a main part of a capsule endoscope according to an embodiment of the present invention.

FIG. 1 is a diagram showing a configuration of a main part of a capsule endoscope according to the embodiment of the present invention.

A capsule endoscope 1001 is configured to be capable of moving according to peristaltic movement of a digestive tract. The capsule endoscope 1001 includes, as shown in FIG. 1, a housing 1002 of a capsule type, excitation light emitting sections 1003 that are housed in the housing 1002 and irradiate excitation light via a transparent window 1002b, an image pickup section 1005 that picks up an image of a site to be observed in a body cavity and outputs an image pickup signal, an image generating section 1006 that applies various kinds of image processing to the image pickup signal outputted from the image pickup section 1005 and generates image data, a radio transmission section 1007a capable of transmitting a radio signal to an outside of the housing 1002, a radio reception section 1007b capable of receiving a radio signal transmitted from the outside of the housing 1002, a control section 1008 that performs control and the like for the respective sections of the capsule endoscope 1001, and a battery 1009 capable of supplying driving power for driving the respective sections of the capsule endoscope 1001. In FIG. 1, for simplification, wires from the battery 1009 to the respective sections of the capsule endoscope 1001 are not shown.

The housing 1002 of the capsule type is formed by sealing both ends of a cylindrical housing body 1002a with a semispherical transparent window 1002b and a semispherical end plate 1002c.

The excitation light emitting sections 1003 include light emitting diodes (hereinafter abbreviated as LEDs 1003a that emit lights in wavelength ranges including a visible range or a near infrared range and excitation light filters 1003b arranged in front of light-emitting surfaces of the LEDs 1003a and formed to include a characteristic for allowing light in a part of the visible range or in a red range to pass.

Specifically, the excitation light filters 1003b are formed to allow, for example, light in a wavelength band of 600 to 650 nm among lights in respective wavelength bands emitted from the LEDs 1003a to pass without generally attenuating the light.

Figure 2:
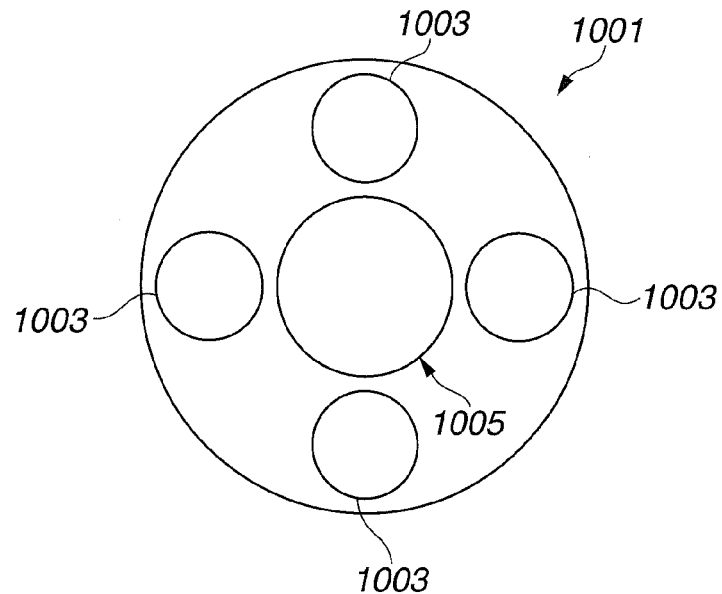
FIG. 2 is a diagram showing an example of positions where excitation light illumination sections and an image pickup section are arranged in the capsule endoscope shown in FIG. 1.

FIG. 2 is a diagram showing an example of positions where the excitation light illumination sections and the image pickup section are arranged in the capsule endoscope shown in FIG. 1.

The excitation light emitting sections 1003 of the capsule endoscope 1001 are not limited to four excitation light emitting sections arranged around the image pickup section 1005, for example, as shown in FIG. 2. The excitation light emitting sections 1003 may be arranged around the image pickup section 1005 in any number equal to or larger than one.

The image pickup section 1005 includes an objective optical system 1005a that condenses return light made incident on an inside of the housing 1002 via the transparent window 1002b, an excitation light cut filter 1005b formed to include a characteristic for blocking light in a wavelength band of excitation light, and an image pickup device 1005c such as a highly sensitive CCD capable of picking up an image of light passed through the objective optical system 1005a and the excitation light cut filter 1005b and outputting an image pickup signal.

Specifically, the excitation light cut filter 1005b is formed to allow, for example, only light in 680 to 800 nm among lights made incident through the objective optical system 1005a to pass without generally attenuating the light.

The radio transmission section 1007a is configured to be capable of applying signal processing such as modulation to image data generated by the image generating section 1006 to thereby generate a radio signal and transmitting the generated radio signal to the outside of the housing 1002.

The radio reception section 1007b is configured to be capable of receiving a radio signal transmitted from the outside of the housing 1002 and outputting information and the like obtained by applying signal processing such as demodulation to the received radio signal to the control section 1008.

Figure 3:
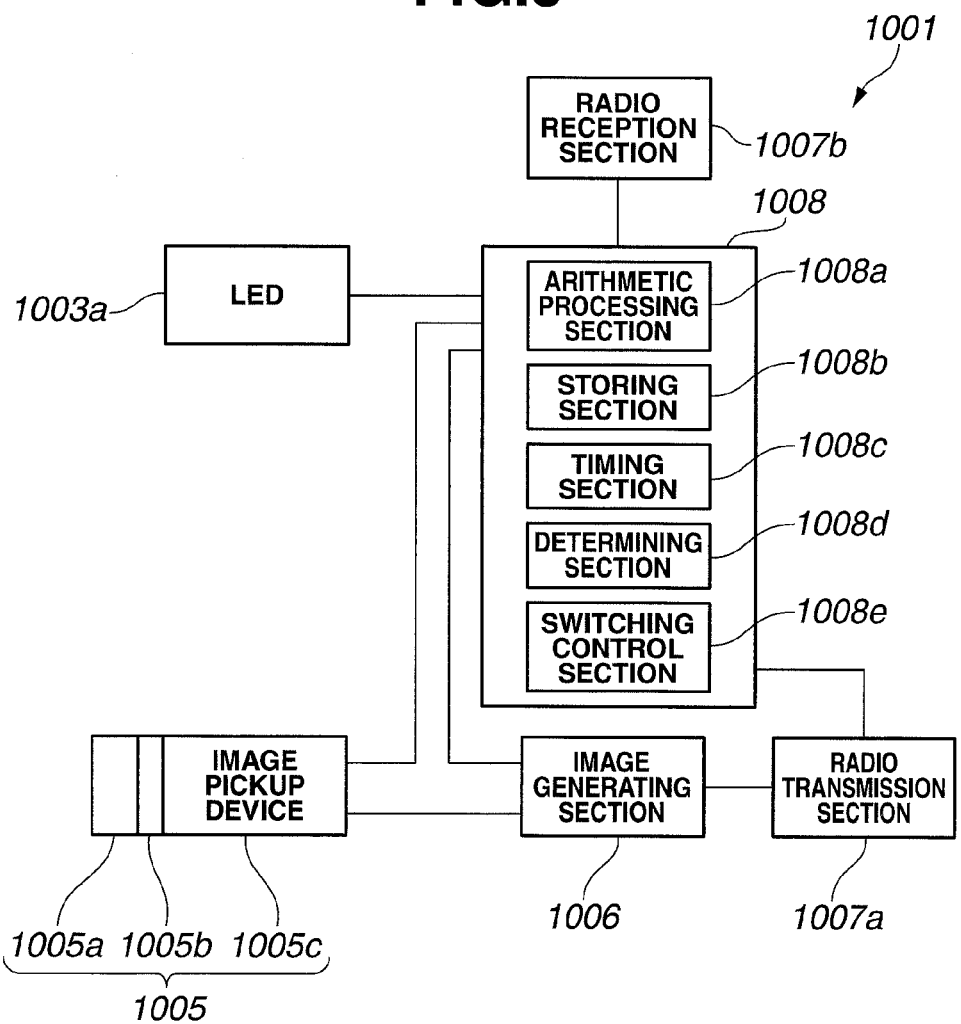
FIG. 3 is a block diagram showing a configuration of a main part of the capsule endoscope shown in FIG. 1.

FIG. 3 is a block diagram showing a configuration of a main part of the capsule endoscope shown in FIG. 1. In FIG. 3, for simplification, a part of a configuration of the capsule endoscope 1001 is not shown.

The control section 1008 including a central processing unit (hereinafter abbreviated as CPU) and a memory includes, as shown in FIG. 3, an arithmetic processing section 1008a that performs arithmetic processing, a storing section 1008b, a timing section 1008c, a determining section 1008d, and a switching control section 1008e. (The switching control section 1008e of) The control section 1008 causes the respective sections to operate based on information and the like outputted from the radio reception section 1007b to thereby apply control explained below to the respective sections of the capsule endoscope 1001. Further, the control section 1008 performs, in parallel to the above-mentioned control, processing for giving, to the image data generated by the image generating section 1006, information concerning an acquisition time of the image data, below-mentioned position information, and the like as additional information.

In the storing section 1008b, various data used for, for example, arithmetic processing of the arithmetic processing section 1008a such as below-mentioned table data are stored.

The timing section 1008c includes an RTC (real time clock) and a timer. The timing section 1008c is configured be capable of measuring an elapsed time from administration of a fluorescent drug to a subject.

The determining section 1008d performs determination processing explained below based on an arithmetic processing result of the arithmetic processing section 1008a and a measurement result of the timing section 1008c.

The switching control section 1008e applies control based on a determination result of the determining section 1008d to the respective sections of the capsule endoscope 1001.

Figure 4:
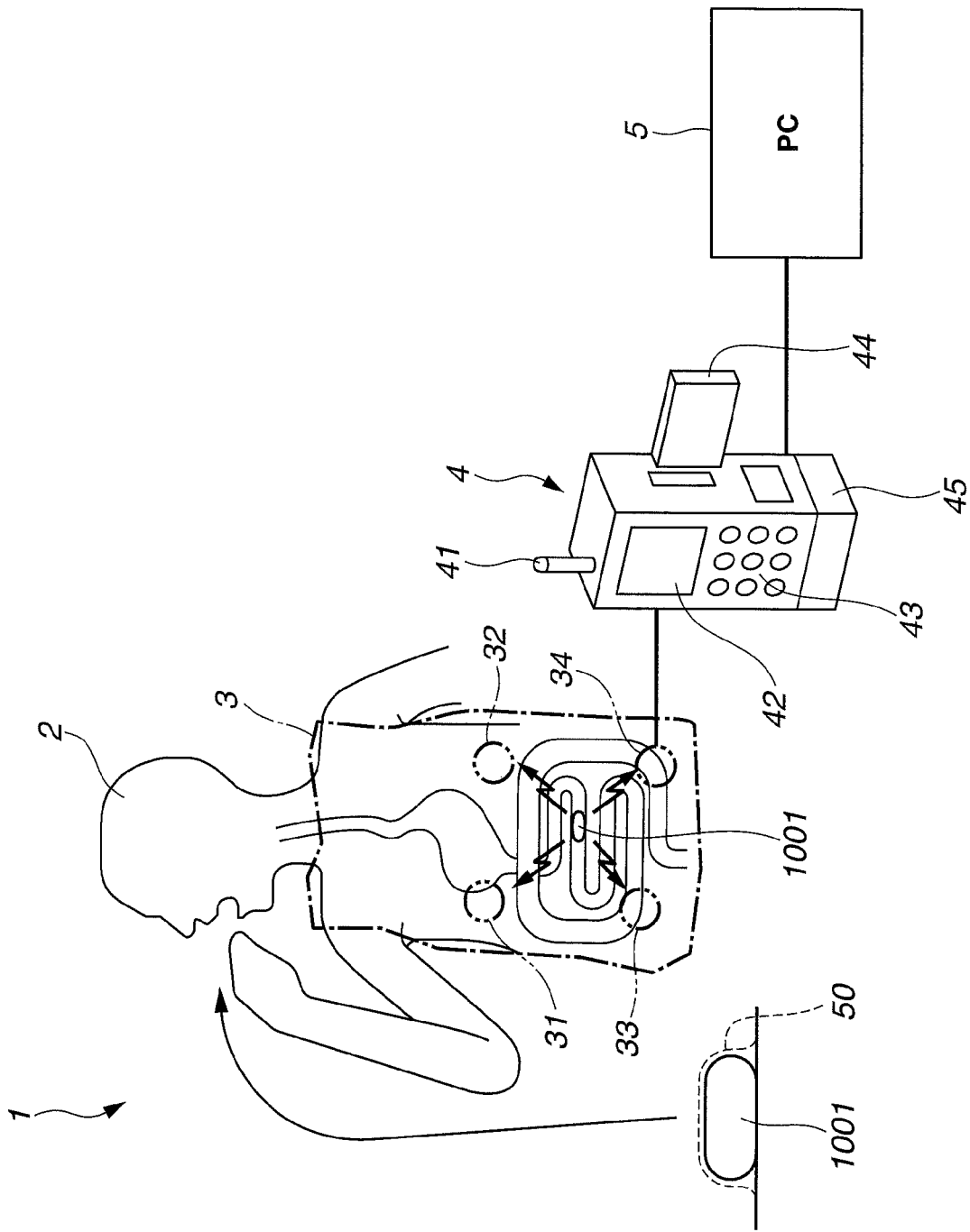
FIG. 4 is a diagram showing a configuration of a main part of a capsule endoscope system including the capsule endoscope shown in FIG. 1.
Figure 5:
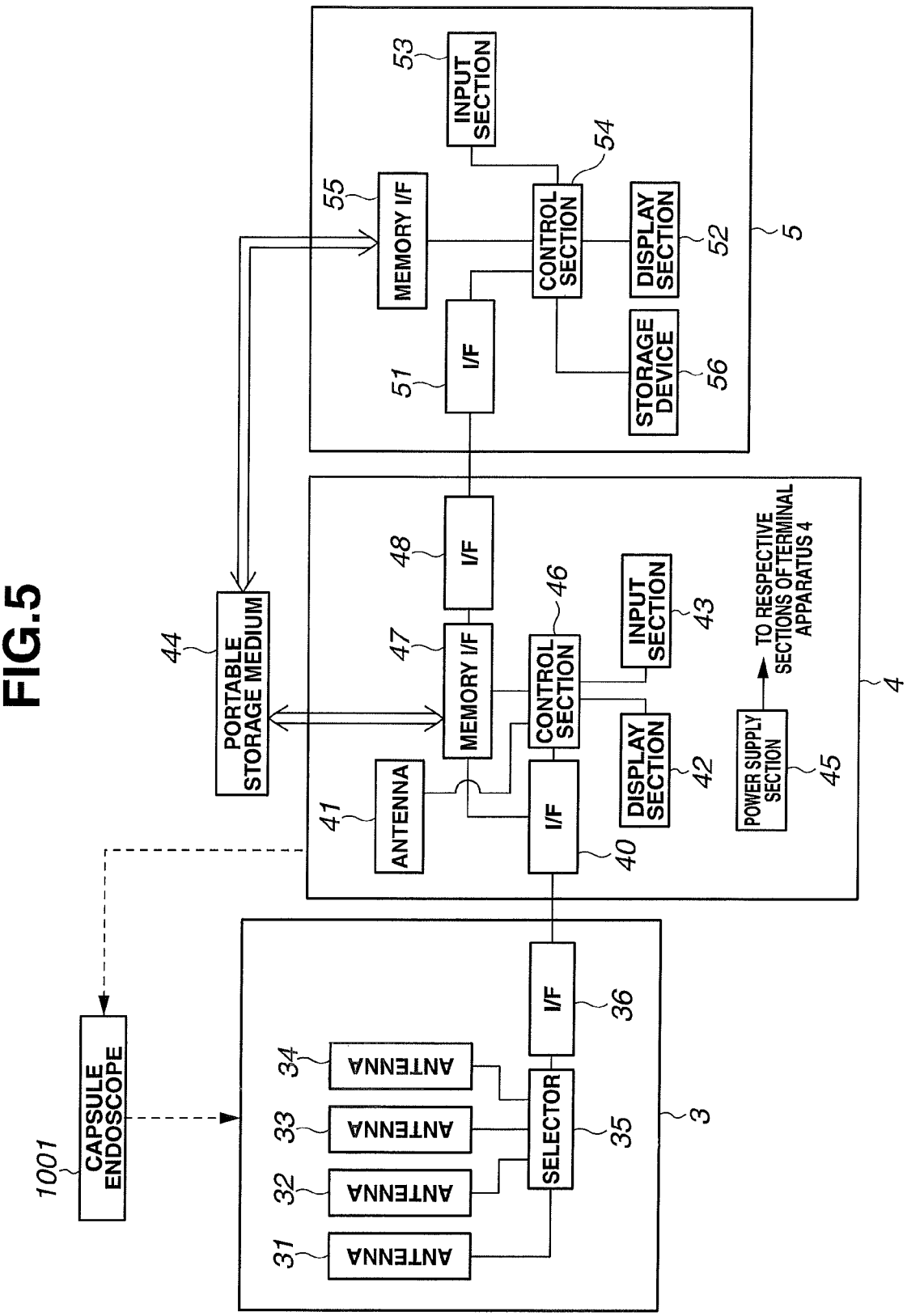
FIG. 5 is a block diagram showing a configuration of a main part of the capsule endoscope system shown in FIG. 4.

FIG. 4 is a diagram showing a configuration of a main part of a capsule endoscope system including the capsule endoscope shown in FIG. 1. FIG. 5 is a block diagram showing a configuration of a main part of the capsule endoscope system shown in FIG. 4.

A capsule endoscope system 1 includes, as shown in FIG. 4, the capsule endoscope 1001 arranged in a body cavity of a subject 2 by being swallowed in a state in which the capsule endoscope 1001 is taken out from a package 50 for storage, a jacket 3 worn by the subject 2, a terminal apparatus 4 configured to be detachably attachable to the jacket 3, and a personal computer (hereinafter abbreviated as PC) 5.

In the jacket 3, as shown in FIG. 4, antennas 31, 32, 33, and 34, which include, for example, three-axis coils, capable of receiving a radio signal transmitted from the capsule endoscope 1001 in positions different from each other are provided. With such a configuration, a radio signal transmitted according to movement of the capsule endoscope 1001 can be received in four places of the jacket 3 for each of components in respective directions (e.g., an X axis direction, a Y axis direction, and a Z axis direction of an orthogonal coordinate system) of three axis directions.

The number of antennas provided in the jacket 3 may be a number other than four as long as plural antennas are provided.

Further, in the jacket 3, as shown in FIG. 5, a selector 35 connected to each of the antennas 31 32, 33, and 34 and an interface (hereinafter abbreviated as I/F) 36 to which a cable for communication for connecting the jacket 3 to the terminal apparatus 4 is detachably attachable are provided.

The selector 35 selects one antenna having a highest reception level (reception intensity) of a radio signal out of the antennas 31, 32, 33, and 34 and outputs a signal received in the selected one antenna to the terminal apparatus 4 via the cable for communication attached to the I/F 36.

The terminal apparatus 4 is configured as a portable terminal that can be carried in a state in which the terminal is connected to the jacket 3. The terminal apparatus 4 includes, as shown in FIGS. 4 and 5, an I/F 40 to which a cable for communication for connecting the terminal apparatus 4 to the jacket 3 is detachably attachable, an antenna 41 capable of outputting a radio signal to the capsule endoscope 1001, a display section 42 capable of displaying information and the like concerning an observation (a test), an input section 43 to which information and the like concerning an observation (a test) can be inputted, a power supply section 45 including a battery or the like capable of supplying driving power for driving the respective sections of the terminal apparatus 4, a control section 46 that performs controls and the like for the respective sections of the terminal apparatus 4, a memory I/F 47, and an I/F 48 to which a cable for communication for connecting the terminal apparatus 4 to the PC 5 is detachably attachable.

The antenna 41 is configured to generate a radio signal corresponding to information outputted from the control section 46 and output the generated radio signal to the capsule endoscope 1001.

The control section 46 including a CPU and a memory acquires information inputted in the input section 43 when an observation is carried out using the capsule endoscope 1001. The control section 46 causes the antenna 41 to output the acquired information to the capsule endoscope 1001. Details of the information inputted in the input section 43 when the observation is carried out using the capsule endoscope 1001 are explained below.

The control section 46 can acquire, based on an output signal outputted from the I/F 40 during the observation carried out using the capsule endoscope 1001, substantially on a real time, position information indicating a present position of the capsule endoscope 1001 (e.g., in which organ or body part the capsule endoscope 1001 is located). The control section 46 causes the antenna 41 to output the acquired position information to the capsule endoscope 1001. Therefore, according to the present embodiment, the radio reception section 1007b of the capsule endoscope 1001 can receive a radio signal including the position information of the capsule endoscope 1001. The radio reception section 1007b can acquire the position information of the capsule endoscope 1001 by applying signal processing such as demodulation to the received radio signal. Further, the acquired position information of the capsule endoscope 1001 is outputted to the control section 1008.

The position information acquired by the control section 46 in the present embodiment can be used as position information indicating a present position of any one of the respective sections of the capsule endoscope 1001 as well. Specifically, the position information acquired by the control section 46 in the present embodiment can be used as, for example, position information indicating a present position of the image pickup section 1005 of the capsule endoscope 1001 as well. Therefore, in the present embodiment, the position information indicating the present position of the capsule endoscope 1001 and the position information indicating the present position of the image pickup section 1005 are substantially synonymous.

Further, the control section 46 can cause the display section 42 to display, based on the output signal outputted from the I/F 40 during the observation carried out using the capsule endoscope 1001, on substantially a real time basis, image data acquired by the capsule endoscope 1001.

The memory I/F 47 is connected to each of the I/F 40 and the I/F 48. The memory I/F 47 includes a configuration to which a portable storage medium 44 such as a memory card is detachably attachable.

The PC 5 includes an I/F 51 to which a cable for communication for connecting the PC 5 to the terminal apparatus 4 is detachably attachable, a display section 52 capable of displaying information and the like concerning an observation (a test), an input section 53 to which information and the like concerning an observation (a test) can be inputted, a control section 54 that performs control and the like for the respective sections of the PC 5, a memory I/F 55 including a configuration to which the portable storage medium 44 is detachably attachable, and a storage device 56 including a hard disk drive and the like.

The control section 54 including a CPU and a memory can store (information and the like included in) an output signal outputted from the I/F 51 during the observation carried out using the capsule endoscope 1001 in the storage device 56 substantially on a real time basis.

With the configurations of the terminal apparatus 4 and the PC 5 explained above, it is possible to store (information and the like included in) the output signal outputted from the I/F 40 during the observation carried out using the capsule endoscope 1001 in both of the portable storage medium 44 and the storage device 56 on substantially a real time basis. With the configurations of the terminal apparatus 4 and the PC 5 explained above, it is possible to store (the information and the like included in) the output signal outputted from the I/F 40 during the observation carried out using the capsule endoscope 1001 in the portable storage medium 44 on substantially a real time basis. Further, after the observation carried out using the capsule endoscope 1001, the portable storage medium 44 is detached from the memory I/F 47 and attached to the memory I/F 55, whereby it is possible to cause the control section 54 to read image data and the like stored in the portable storage medium 44.

Figure 6:
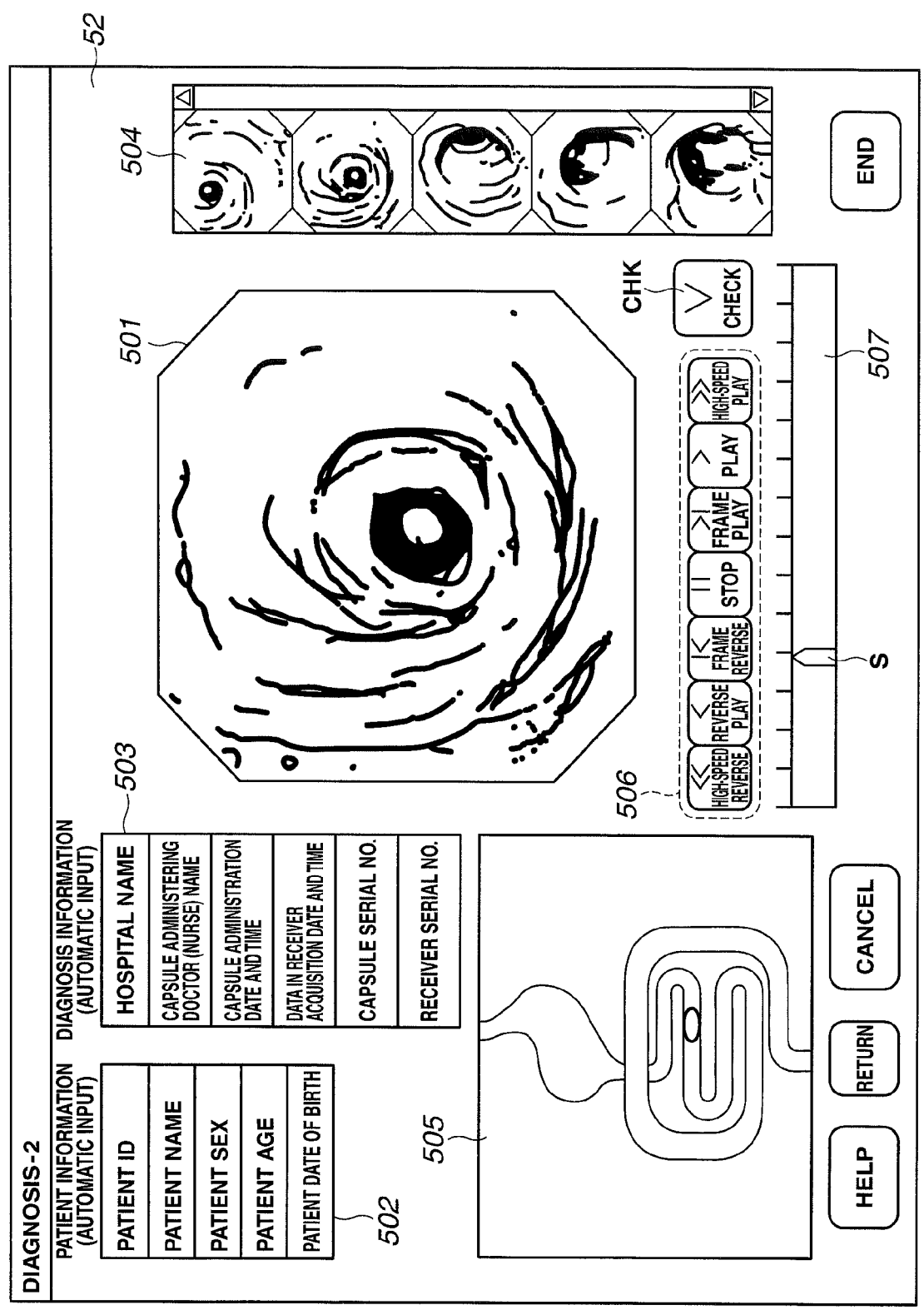
FIG. 6 is a diagram showing an example of a reproduction and display screen for image data.

On the other hand, the control section 54 generates, based on input content and the like in the input section 53, for example, a reproduction and display screen shown in FIG. 6 as a screen for reading and reproducing and displaying image data stored in the portable storage medium 44 attached to the memory I/F 55 or image data stored in the storage device 56 and causes the display section 52 to display the reproduction and display screen.

FIG. 6 is a diagram showing an example of the reproduction and display screen for image data.

On the reproduction and display screen illustrated in FIG. 6, an image display space 501 for displaying one of respective image data acquired by the capsule endoscope 1001, a patient information display space 502 for displaying information concerning a patient from whom the image data displayed in the image display space 501 is acquired, and a diagnosis information display space 503 for displaying information concerning diagnosis at the time when the image data displayed in the image display space 501 is acquired are arranged.

On the reproduction and display screen illustrated in FIG. 6, a check image display space 504 for listing image data arbitrarily checked (selected) by operation of a check button CHK, a 3D position display space 505 capable of three-dimensionally displaying a position in a body cavity at the time when the image data displayed in the image display space 501 is acquired, a reproducing operation space 506 for performing reproducing operation for the image data displayed in the image display space 501, and a time bar 507 indicating an elapsed time from an observation start time (an acquisition start time for the image data) are arranged.

Further, on the reproduction and display screen illustrated in FIG. 6, a help button capable of switching help functions for respective kinds of information displayed in the screen to be active or inactive, a cancel button capable of initializing the respective kinds of information displayed in the screen, and an end button for closing the screen and ending the reproduction and display are arranged.

In the reproducing operation space 506, a frame play button, a play button, and a high-speed play button capable of reproducing and displaying the image data displayed in the image display space 501 while switching the image data in a forward direction along time series are arranged. In the reproducing operation space 506, a frame reverse play button, a reverse play button, and a high-speed reverse play button capable of reproducing and displaying the image data displayed in the image display space 501 while switching the image data in a reverse direction along time series are arranged. Further, in the reproducing operation space 506, a stop button capable of stopping the switching display of the image data displayed in the image display space 501 is arranged.

In the time bar 507, a slider S that moves in a time axis direction in association with each of the operation of the respective buttons of the reproducing operation space 506 and the switching of the image data displayed in the image display space 501 is arranged.

With the reproduction and display screen explained above, it is possible to easily grasp a correspondence relation between image data acquired by the capsule endoscope 1001 and a situation (an image pickup position, an image pickup time, etc.) at the time when the image data is acquired.

Subsequently, action of the present embodiment is explained.

First, a surgeon or the like connects the terminal apparatus 4, in which the portable storage medium 44 is inserted, to the jacket 3 and causes the subject 2 to wear the jacket 3. After taking out the capsule endoscope 1001 from the package 50 for storage, the surgeon or the like turns on a power supply for the respective sections of the capsule endoscope system 1. The surgeon or the like administers a fluorescent drug to a site to be observed of the subject 2 and leads the capsule endoscope 1001 into the subject 2.

Subsequently, the surgeon or the like operates switches and the like of the input section 43 to thereby (for, example, cause the display section 42 to display a setting screen related to various kinds of setting of the terminal apparatus 4 and) respectively set a reference value Ns of an accumulation amount at diagnosis start time, a reference value Ne of an accumulation amount at diagnosis end time, a type of the fluorescent drug in use, a body part to which a target region (a site to be observed) administered with the fluorescent drug belongs, a method of administering the fluorescent drug to the target region, and an administration start time of the fluorescent drug to the subject 2 in an observation carried out using the fluorescent drug.

The reference values Ns and Ne are values indicating a ratio with respect to 100% set as a maximum value Nmax equivalent to a peak value of an accumulation amount of the fluorescent drug. In an initial state, the reference values Ns and Ne are stored in the storing section 1008b of the capsule endoscope 1001 in a state in which the reference values Ns and Ne are set as Ns=Ne=Nmax.

Depending on a way of combining a type of a fluorescent drug in use, a body part to which a target region administered with the fluorescent drug belongs, and a method of administering the fluorescent drug to the target region, a sufficient diagnosis ability can be sometimes obtained even if the reference values Ns and Ne are respectively values other than Nmax. Therefore, the reference values Ns and Ne may be able to be respectively set to arbitrary values by the operation of the input section 43 or may be able to be selected one by one out of predetermined plural values (such as 80%, 60%, and the like).

When the control section 46 detects that the above-mentioned respective kinds of information are inputted in the input section 43, the control section 46 causes the antenna 41 to transmit a radio signal including the inputted respective kinds of information to the capsule endoscope 1001.

On the other hand, when the control section 1008 detects, based on information outputted from the radio reception section 1007b, that new reference values Ne and Ns are set, the control section 1008 updates the reference values Ns and Ne stored in the storing section 1008b.

The arithmetic processing section 1008a of the control section 1008 selects, based on the information outputted from the radio reception section 1007b, one table data coinciding with the type of the fluorescent drug in use out of the table data stored in advance in the storing section 1008b.

FIG. 7 is a diagram showing an example of table data used in selecting a drug movement of a fluorescent drug.

In the table data, for example, as shown in FIG. 7, information concerning drug movements in a living body are stored in advance in the storing section 1008b in a state in which the information is classified for each of types of plural fluorescent drugs.

When the fluorescent drug in use is a fluorescent drug A, the arithmetic processing section 1008a of the control section 1008 selects the table data illustrated in FIG. 7.

Further, the arithmetic processing section 1008a of the control section 1008 selects, out of the selected one table data, one drug movement corresponding to a combination of a body part to which a target region administered with the fluorescent drug belongs and a method of administering the fluorescent drug to the target region.

Specifically, for example, in the table data shown in FIG. 7, when the target region administered with the fluorescent drug belongs to a stomach and the fluorescent drug is administered by intravenous injection, the arithmetic processing section 1008a of the control section 1008 selects a drug movement A02.

According to the present embodiment, for example, the reference values Ns and Ne are set in advance for each of the drug movements in the respective table data stored in the storing section 1008b, whereby the reference values Ns and Ne may be uniquely decided according to selection of one drug movement.

The arithmetic processing section 1008a of the control section 1008 causes, based on the reference values Ns and Ne stored in the storing section 1008b and an administration start time of the fluorescent drug to the subject 2, a point when the elapsed time T from the administration of the fluorescent drug to the subject 2 is 0 and the accumulation amount N of the fluorescent drug is 0 to coincide with the administration start time in the one drug movement selected by the above-mentioned processing, acquires a diagnosis start time Ts equivalent to the first elapsed time T when the accumulation amount N is equal to Ns, and acquires a diagnosis end time Te equivalent to the elapsed time T when the accumulation amount N is equal to Ne last after the diagnosis start time Ts.

FIG. 8 is a diagram showing an example of a drug movement selected out of the table data. FIG. 9 is a diagram showing an example of a diagnosis start time and a diagnosis end time acquired when the drug movement shown in FIG. 8 is selected.

A drug movement of a fluorescent drug in a living body has, for example, a correlation shown in FIG. 8 between the elapsed time T from administration of the fluorescent drug into a body of the subject until the fluorescent drug is discharged and the accumulation amount N in a target region in the body of the subject administered with the fluorescent drug. Therefore, for example, when the drug movement shown in FIG. 8 is selected as a drug movement of the fluorescent drug and both the reference values Ns and Ne are set as Nmax, the diagnosis start time Ts and the diagnosis end time Te shown in FIG. 9 are acquired.

On the other hand, the determining section 1008d of the control section 1008 performs, based on the diagnosis start time Ts and the diagnosis end time Te acquired by the arithmetic processing section 1008a and a measurement result of the timing section 1008c, determination concerning whether a current time is equivalent to time within a diagnosis available time, which is a period of time from the diagnosis start time Ts to the diagnosis end time Te. In other words, the determining section 1008d of the control section 1008 performs, based on the diagnosis start time Ts and the diagnosis end time Te acquired by the arithmetic processing section 1008a and the measuring result of the timing section 1008c, determination concerning whether the current time reaches the diagnosis start time Ts and determination concerning whether the current time reaches the diagnosis end time Te.

When a determination result that the current time is not within the diagnosis available time is obtained by the determining section 1008d, the switching control section 1008e of the control section 1008 performs control to cause the respective LEDs 1003a of the excitation light emitting sections 1003 to extinguish light, stop driving of the image pickup device 1005c of the image pickup section 1005, cause the image generating section 1006 to generate blank image data such as a single color image, and cause the radio transmission section 1007a to transmit the generated blank image data.

In other words, when it is determined that the current time is not within the diagnosis available time, the control section 46 acquires, based on an output signal from the I/F 40 including the blank image data, position information indicating a present position of the capsule endoscope 1001. Further, the acquired position information is transmitted to the capsule endoscope 1001.

When a determination result that the current time is within the diagnosis available time is obtained, the determining section 1008d of the control section 1008 further performs, based on position information outputted from the radio reception section 1007b, determination concerning whether the capsule endoscope 1001 reaches a periphery of a site to be observed.

When a determination result that the capsule endoscope 1001 does not reach the periphery of the site to be observed is obtained by the determining section 1008d, the switching control section 1008e of the control section 1008 performs control to cause the respective LEDs 1003a of the excitation light emitting sections 1003 to extinguish light, stop driving of the image pickup device 1005c of the image pickup section 1005, cause the image generating section 1006 to generate blank image data such as a single color image, and cause the radio transmission section 1007a to transmit the generated blank image data.

In other words, when it is determined that the current time is within the diagnosis available time and the capsule endoscope 1001 does not reach the periphery of the site to be observed, the control section 46 acquires, based on an output signal from the I/F 40 including the blank image data, position information indicating a present position of the capsule endoscope 1001. Further, the acquired position information is transmitted to the capsule endoscope 1001.

When a determination result that the capsule endoscope 1001 reaches the periphery of the site to be observed is obtained by the determining section 1008d, the switching control section 1008e of the control section 1008 performs control to cause the respective LEDs 1003a of the excitation light emitting sections 1003 to emit light, drive the image pickup device 1005c of the image pickup section 1005, cause the image generating section 1006 to generate image data corresponding to an image pickup signal outputted from the image pickup section 1005, and cause the radio transmission section 1007a to transmit the generated image data.

In other words, when it is determined that the current time is within the diagnosis available time and the capsule endoscope 1001 reaches the periphery of the site to be observed, the control section 46 acquires, based on an output signal from the I/F 40 including image data obtained by picking up an image of fluorescence emitted from the fluorescent drug, position information indicating a present position of the capsule endoscope 1001. Further, the acquired position information is transmitted to the capsule endoscope 1001.

Figure 10:
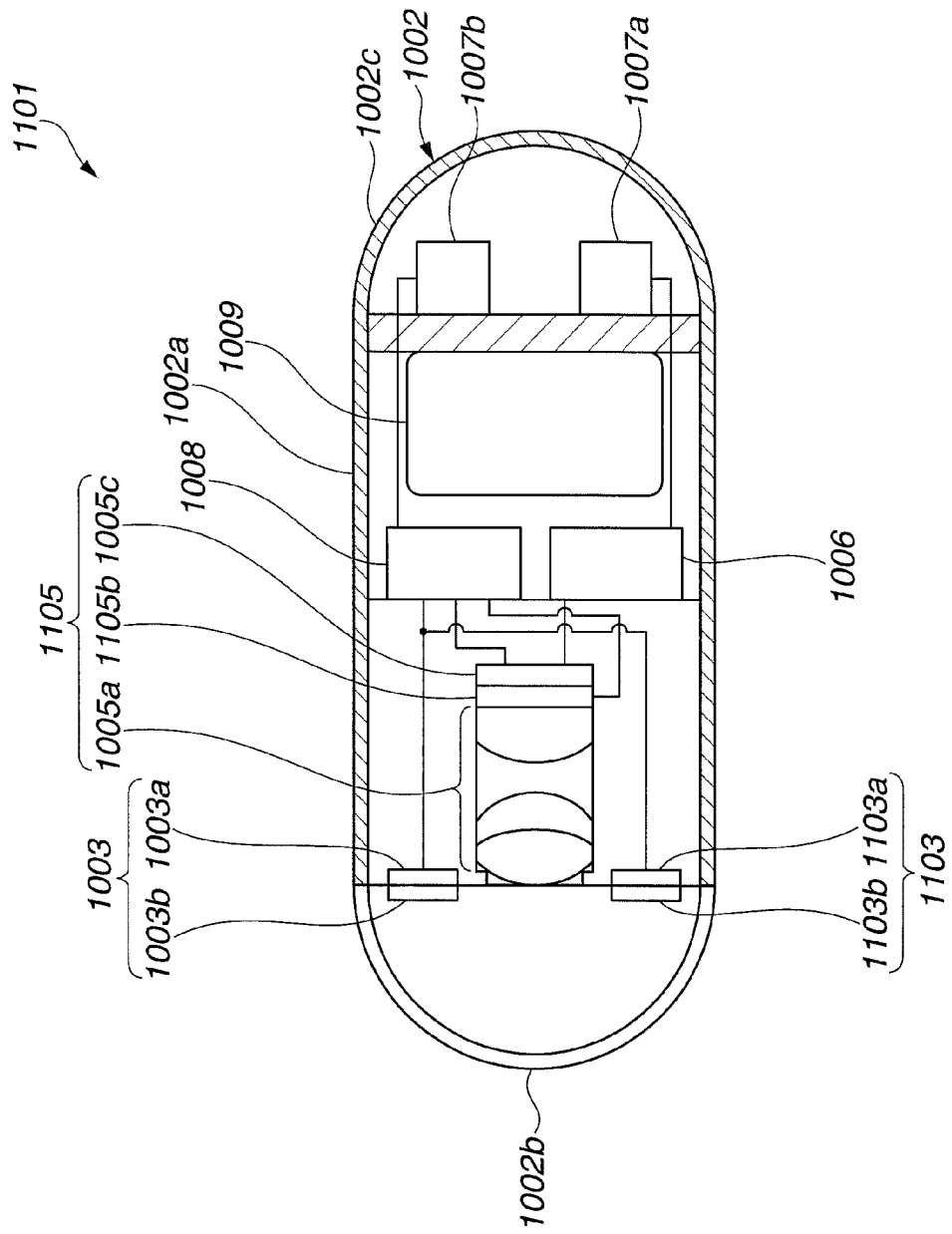
FIG. 10 is a diagram showing a configuration of a main part of a capsule endoscope according to a modification of the embodiment of the present invention.

In the present embodiment, a capsule endoscope 1101 shown in FIG. 10 may be used instead of using the capsule endoscope 1001 illustrated in FIG. 1.

FIG. 10 is a diagram showing a configuration of a main part of a capsule endoscope according to a modification of the embodiment of the present invention.

The capsule endoscope 1101 includes, as shown in FIG. 10, the housing 1002, the excitation light emitting sections 1003, white color light emitting sections 1103 that are housed in the housing 1002 and irradiate white color light via the transparent window 1002b, an image pickup section 1105, the image generating section 1006, the radio transmission section 1007a, the radio reception section 1007b, the control section 1008, and the battery 1009. In FIG. 10, for simplification, wires from the battery 1009 to the respective sections of the capsule endoscope 1101 are not shown.

The white color light emitting sections 1103 include LEDs 1103a that emit light in a wavelength band same as the wavelength band of the LEDs 1003a and white color light filters 1103b arranged in front of light-emitting surfaces of the LEDs 1103a and formed to include a characteristic for allowing light in the visible range to pass.

Specifically, the white color light filters 1103b are formed to allow, for example, light in a wavelength band of 400 to 650 nm among lights in respective wavelength bands emitted from the LEDs 1103a to pass without generally attenuating the light.

Figure 11:
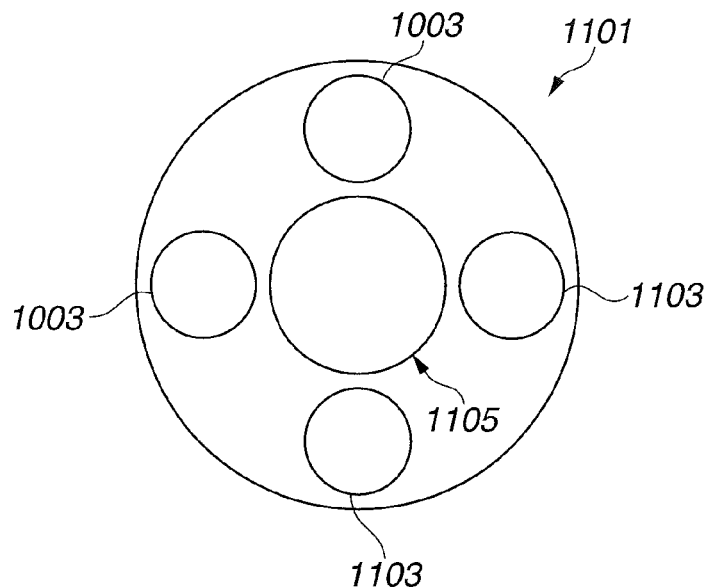
FIG. 11 is a diagram showing an example of positions where excitation light illumination sections, white color light illumination sections, and an image pickup section are arranged in the capsule endoscope shown in FIG. 10.

FIG. 11 is a diagram showing an example of positions where the excitation light illumination sections, the white color light illumination sections, and the image pickup section are arranged in the capsule endoscope shown in FIG. 10.

The excitation light emitting sections 1003 and the white color light emitting sections 1103 of the capsule endoscope 1101 are not limited to two excitation light emitting sections 1003 and two white color light emitting sections 1103 arranged around the image pickup section 1105, for example, as shown in FIG. 11. The excitation light emitting sections 1003 and the white color light emitting sections 1103 may be each arranged around the image pickup section 1105 in any number equal to or larger than one.

The image pickup section 1105 includes the objective optical system 1005a, the image pickup device 1005c, and a filter switching section 1105b arranged on an optical path between the objective optical system 1005a and the image pickup device 1005c.

Figure 12:
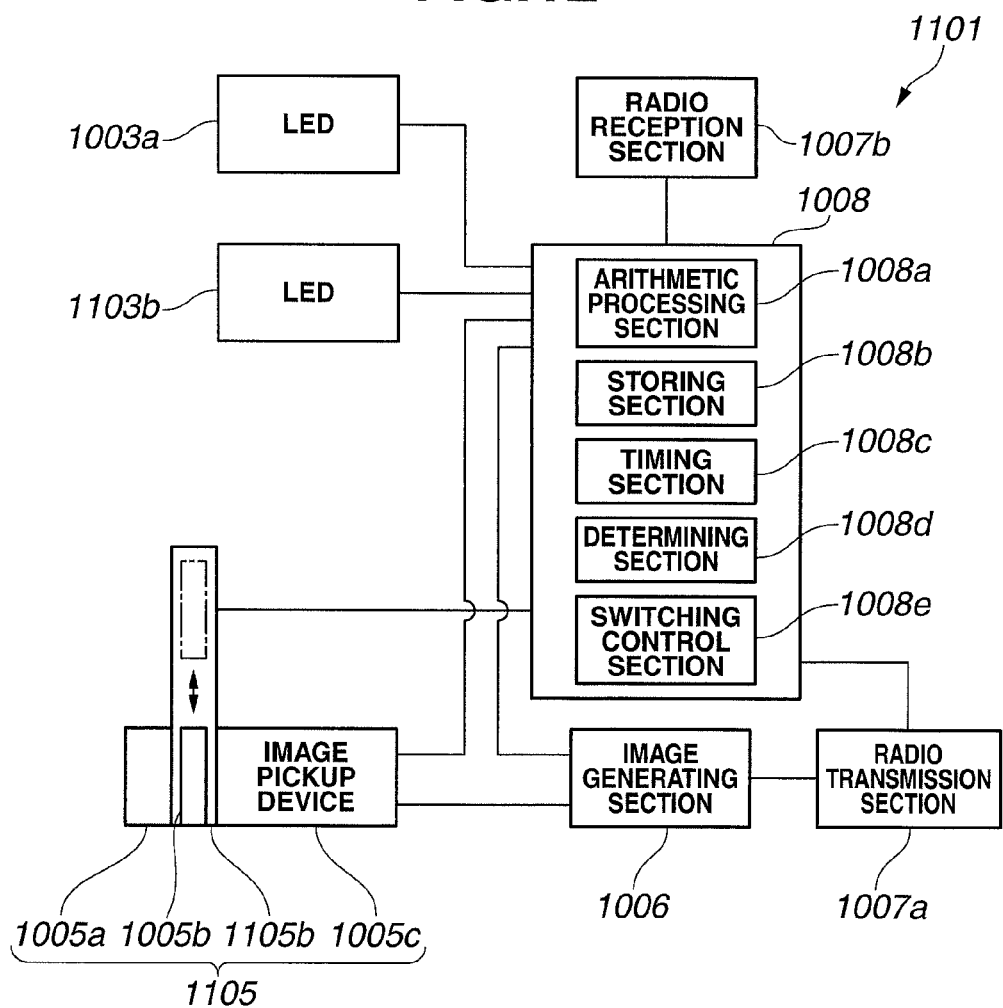
FIG. 12 is a block diagram showing a configuration of a main part of the capsule endoscope shown in FIG. 10.

FIG. 12 is a block diagram showing a configuration of a main part of the capsule endoscope shown in FIG. 10. In FIG. 12, for simplification, a part of a configuration of the capsule endoscope 1101 is not shown.

The filter switching section 1105b includes, for example, as shown in FIG. 12, a configuration capable of switching, according to control by the control section 1008, a state in which the excitation light cut filter 1005b is interposed on an optical path extending from the objective optical system 1005a to the image pickup device 1005c and a state in which the excitation light cut filter 1005b is retracted from the optical path extending from the objective optical system 1005a to the image pickup device 1005c.

In other words, the image pickup section 1105 is configured to be capable of focusing light passed through the objective optical system 1005a and the excitation light cut filter 1005b on the image pickup device 1005c in the state in which the excitation light cut filter 1005b of the filter switching section 1105b is interposed on the optical path extending from the objective optical system 1005a to the image pickup device 1005c. Further, the image pickup section 1105 is configured to be capable of focusing light passed through the objective optical system 1005a on the image pickup device 1005c in the state in which the excitation light cut filter 1005b of the filter switching section 1105b is retracted from the optical path extending from the objective optical system 1005a to the image pickup device 1005c.

The filter switching section 1105b of the image pickup section 1105 may be any filter switching section as long as the filter switching section includes the configuration capable of switching the two states.

Subsequently, action of the modification of the present embodiment is explained while the contents already explained are omitted as appropriate.

First, the surgeon or the like connects the terminal apparatus 4, in which the portable storage medium 44 is inserted, to the jacket 3 and causes the subject 2 to wear the jacket 3. After taking out the capsule endoscope 1101 from the package 50 for storage, the surgeon or the like turns on the power supply for the respective sections of the capsule endoscope system 1. The surgeon or the like administers a fluorescent drug to a site to be observed of the subject 2 and leads the capsule endoscope 1101 into the subject 2.

Subsequently, the surgeon or the like operates the switches and the like of the input section 43 to thereby (for, example, cause the display section 42 to display the setting screen related to various kinds of setting of the terminal apparatus 4 and) respectively set the reference value Ns of an accumulation amount at diagnosis start time, the reference value Ne of an accumulation amount at diagnosis end time, a type of the fluorescent drug in use, a body part to which a target region (a site to be observed) administered with the fluorescent drug belongs, a method of administering the fluorescent drug to the target region, and an administration start time of the fluorescent drug to the subject 2 in an observation carried out using the fluorescent drug.

When the control section 46 detects that the above-mentioned respective kinds of information are inputted in the input section 43, the control section 46 causes the antenna 41 to transmit a radio signal including the inputted respective kinds of information to the capsule endoscope 1101.

On the other hand, when the control section 1008 detects, based on information outputted from the radio reception section 1007b, that new reference values Ne and Ns are set, the control section 1008 updates the reference values Ns and Ne stored in the storing section 1008b.

The arithmetic processing section 1008a of the control section 1008 selects, based on the information outputted from the radio reception section 1007b, one table data coinciding with the type of the fluorescent drug in use out of the table data of the plural fluorescent drugs stored in advance in the storing section 1008b. Thereafter, the arithmetic processing section 1008a of the control section 1008 further selects, out of the selected one data table, one drug movement corresponding to a combination of the body part to which the target region (the site to be observed) administered with the fluorescent drug belongs and the method of administering the fluorescent drug to the garget region.

The arithmetic processing section 1008a of the control section 1008 causes, based on the reference values Ns and Ne stored in the storing section 1008b and an administration start time of the fluorescent drug to the subject, a point when the elapsed time T from the administration of the fluorescent drug to the subject is 0 and the accumulation amount N of the fluorescent drug is 0 to coincide with the administration start time in the one drug movement selected by the above-mentioned processing, acquires the diagnosis start time Ts equivalent to the first elapsed time T when the accumulation amount N is equal to Ns, and acquires the diagnosis end time Te equivalent to the elapsed time T when the accumulation amount N is equal to Ne last after the diagnosis start time Ts.

The determining section 1008d of the control section 1008 performs, based on the diagnosis start time Ts and the diagnosis end time Te acquired by the arithmetic processing section 1008a and a measurement result of the timing section 1008c, determination concerning whether a current time is equivalent to time within a diagnosis available time, which is a period of time from the diagnosis start time Ts to the diagnosis end time Te.

When a determination result that the current time is not within the diagnosis available time is obtained by the determining section 1008d, the switching control section 1008e of the control section 1008 performs control to cause the respective LEDs 1003a of the excitation light emitting sections 1003 to extinguish light, cause the respective LEDs 1103a of the white color light emitting section 1103 to emit light, retract the excitation light cut filter 1005b from the optical path extending from the objective optical system 1005a to the image pickup device 1005c, drive the image pickup device 1005c of the image pickup section 1105, cause the image generating section 1006 to generate image data corresponding to an image pickup signal outputted from the image pickup section 1105, and cause the radio transmission section 1007a to transmit the generated image data.

In other words, when it is determined that the current time is not within the diagnosis available time, the control section 46 acquires, based on an output signal from the I/F 40 including image data obtained by picking up an object illuminated by white color light, position information indicating a present position of the capsule endoscope 1101. Further, the acquired position information is transmitted to the capsule endoscope 1101.

The position information acquired by the control section 46 in this modification can be used as position information indicating a present position of any one of the respective sections of the capsule endoscope 1101 as well. Specifically, the position information acquired by the control section 46 in this modification can be used as, for example, position information indicating a present position of the image pickup section 1105 of the capsule endoscope 1101 as well. Therefore, in this modification, the position information indicating the present position of the capsule endoscope 1101 and the position information indicating the present position of the image pickup section 1105 are substantially synonymous.

When a determination result that the current time is within the diagnosis available time is obtained, the determining section 1008d of the control section 1008 further performs, based on position information outputted from the radio reception section 1007b, determination concerning whether the capsule endoscope 1101 reaches a periphery of a site to be observed.

When a determination result that the capsule endoscope 1101 does not reach the periphery of the site to be observed is obtained by the determining section 1008d, the switching control section 1008e of the control section 1008 performs control to cause the respective LEDs 1003a of the excitation light emitting sections 1003 to extinguish light, cause the respective LEDs 1103a of the white color light emitting sections 1103 to emit light, retract the excitation light cut filter 1005b from the optical path extending from the objective optical system 1005a to the image pickup device 1005c, drive the image pickup device 1005c of the image pickup section 1105, cause the image generating section 1006 to generate image data corresponding to an image pickup signal outputted from the image pickup section 1105, and cause the radio transmission section 1007a to transmit the generated image data.

In other words, when it is determined that the current time is within the diagnosis available time and the capsule endoscope 1101 does not reach the periphery of the site to be observed, the control section 46 acquires, based on an output signal from the I/F 40 including image data obtained by picking up an image of the object illuminated by white color light, position information indicating a present position of the capsule endoscope 1101. Further, the acquired position information is transmitted to the capsule endoscope 1101.

When a determination result that the capsule endoscope 1101 reaches the periphery of the site to be observed is obtained by the determining section 1008d, the switching control section 1008e of the control section 1008 performs control to cause the respective LEDs 1003a of the excitation light emitting sections 1003 to emit light, cause the respective LEDs 1103a of the white color light emitting sections 1103 to extinguish light, interpose the excitation light cut filter 1005b on the optical path extending from the objective optical system 1005a to the image pickup device 1005c, drive the image pickup device 1005c of the image pickup section 1105, cause the image generating section 1006 to generate image data corresponding to an image pickup signal outputted from the image pickup section 1105, and cause the radio transmission section 1007a to transmit the generated image data.

The control section 1008 may be, for example, a control section that performs, in parallel to the control by the switching control section 1008e, processing for acquiring an elapsed time after the respective LEDs 1003a of the excitation light emitting sections 1003 start light emission (an elapsed time after irradiation of excitation light is started) and giving information concerning the elapsed time as additional information of image data generated in the image generating section 1006. The control section 54 of the PC 5 may, for example, color the time bar 507 in the reproduction and display screen shown in FIG. 6 based on presence or absence of such additional information to thereby make it possible to visually distinguish a period in which an image of fluorescence emitted from the fluorescent drug is picked up to obtain image data and a period in which an image of the object illuminated by white color light is picked up to obtain image data.

In other words, when it is determined that the current time is within the diagnosis available time and the capsule endoscope 1101 reaches the periphery of the site to be observed, the control section 46 acquires, based on an output signal from the I/F 40 including image data obtained by picking up an image of fluorescence emitted from the fluorescent drug, position information indicating a present position of the capsule endoscope 1101. Further, the acquired position information is transmitted to the capsule endoscope 1101.

When any one of a determination result that the current time is not within the diagnosis available time, a determination result that the capsule endoscope 1101 does not reach the periphery of the site to be observed, and a determination result that the capsule endoscope 1101 passes the periphery of the site to be observed is obtained by the determining section 1008d, the switching control section 1008e in the present embodiment may perform control to cause the respective LEDs 1003a of the excitation light emitting sections 1003 to extinguish light, cause the respective LEDs 1103a of the white color light emitting section 1103 to emit light, retract the excitation light cut filter 1005b from the optical path extending from the objective optical system 1005a to the image pickup device 1005c, drive the image pickup device 1005c of the image pickup section 1105, cause the image generating section 1006 to generate image data corresponding to an image pickup signal outputted from the image pickup section 1105, and cause the radio transmission section 1007a to transmit the generated image data.

Figure 13:
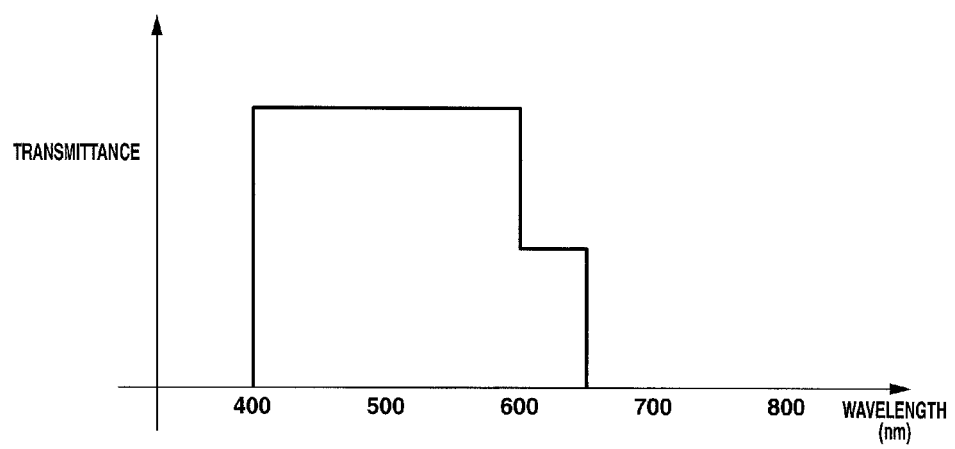
FIG. 13 is a diagram showing an example of characteristics of a filter for discoloration prevention applicable to the capsule endoscope shown in FIG. 10.

In the capsule endoscope 1101, for example, a filter for discoloration prevention including a characteristic shown in FIG. 13 may be provided instead of the white color light filter 1103b.

Specifically, the filter for discoloration prevention including the characteristic illustrated in FIG. 13 allows lights (B light and G light) in a wavelength band equal to or larger than 400 nm and smaller than 600 nm among lights in respective wavelength bands emitted from the LEDs 1103a to pass without generally attenuating the lights and allows light (R light) in a wavelength band equal to or larger than 600 nm and equal to or smaller than 650 nm to pass while attenuating the light to about half intensity. Therefore, when the filter for discoloration prevention including the characteristic illustrated in FIG. 13 is used instead of the white color light filter 1103b, adjustment of a color balance for correcting the attenuation of the intensity of the R light may be performed by the image generating section 1006.

In the capsule endoscope 1101, for example, when the image pickup device 1005c including a charge amplifying device is used, the control section 1008 (the switching control section 1008e) may perform control for changing a driving current for the LEDs 1103a to reduce a light amount in respective wavelength bands of white color light emitted from the white color light emitting section 1103 to a predetermined light amount and control for setting an amplification ratio of the charge amplifying device capable of supplementing such a reduction of the light amount.

As explained above, according to the present embodiment (and the modification of the present embodiment), when fluorescence emitted from the fluorescent drug administered to the site to be observed of the subject is observed, it is possible to suppress as much as possible generation of fluorescence in a period of time other than a period of time in which diagnosis of the site to be observed is possible. Therefore, as a result, it is possible to realize improvement of a diagnosis ability in performing the diagnosis of the site to be observed.

In the capsule endoscope system 1 according to the present embodiment, the position information indicating the present position of the capsule endoscope is not limited to position information obtained from an external apparatus such as the terminal apparatus 4. The capsule endoscope system 1 may be configured such that the capsule endoscope can acquire the position information by itself.

Specifically, for example, the capsule endoscope system 1 may have a configuration in which a pressure sensor capable of detecting pressure applied to the housing 1002 is provided in the capsule endoscope 1001 (the capsule endoscope 1101) and the control section 1008 can obtain position information corresponding to relationship between an output value of the pressure sensor and respective body parts in a body cavity. Alternatively, for example, the capsule endoscope system 1 may have a configuration in which a pH sensor capable of detecting pH of a mucous membrane, which is in contact with the housing 1002, is provided in the capsule endoscope 1001 (the capsule endoscope 1101) and the control section 1008 can obtain position information corresponding to relationship between an output value of the pH sensor and respective body parts in a body cavity.

The capsule endoscope system 1 according to the present embodiment may be configured be capable of guiding the capsule endoscope according to operation of the surgeon or the like by, for example, providing a magnet (not shown) on an inside (of the housing 1002) of the capsule endoscope and providing, on an outside (of the housing 1002) of the capsule endoscope, a magnetic induction device (e.g., a magnetic induction device disclosed in Japanese Patent Application Laid-Open Publication No. 2007-175188) capable of generating a desired magnetic field caused to act on a magnetic field generated from the magnet.

With the configuration in which the magnetic induction device is combined with the capsule endoscope system 1, for example, when the capsule endoscope 1001 (the capsule endoscope 1101) does not reach the periphery of the site to be observed regardless of the fact that the current time is within the diagnosis available time, the surgeon or the like can move the capsule endoscope 1001 (the capsule endoscope 1101) to the site to be observed by causing the magnetic induction device to generate a desired magnetic field while looking at an image displayed on the display section 42 substantially on a real time basis.

With the configuration in which the magnetic induction device is combined with the capsule endoscope system 1, for example, the surgeon or the like can direct an irradiating direction of excitation light, which is emitted from the capsule endoscope 1001 (the capsule endoscope 1101) that reaches the site to be observed, to a direction suitable for an observation by causing the magnetic induction device to generate a desired magnetic field while looking at an image displayed on the display section 42 substantially on a real time basis.

Further, the capsule endoscope system 1 according to the present embodiment may be configured to allow the capsule endoscope to move without making use of a peristaltic movement of a digestive tract by combining a self-propulsion function disclosed in Japanese Patent Application Laid-Open Publication No. 04-176443 with the capsule endoscope system 1.

With the configuration in which the self-propulsion function is combined with the capsule endoscope system 1, for example, when the capsule endoscope 1001 (the capsule endoscope 1101) does not reach the periphery of the site to be observed regardless of the fact that the current time is within the diagnosis available time, the control section 1008 can move the capsule endoscope 1001 (the capsule endoscope 1101) to the site to be observed by causing the self-propulsion function to operate.

With the configuration in which the self-propulsion function is combined with the capsule endoscope system 1, for example, when the capsule endoscope 1001 (the capsule endoscope 1101) passes the periphery of the site to be observed regardless of the fact that the current time is within the diagnosis available time, the control section 1008 can move the capsule endoscope 1001 (the capsule endoscope 1101) to return to the site to be observed by causing the self-propulsion function to operate.

The present invention is not limited to the embodiment explained above. It goes without saying that various modifications and applications are possible without departing from the spirit of the invention.

What is claimed is:

1. A medical apparatus comprising:
    a memory in which information concerning a drug movement in a living body is stored in advance for each of types of a plurality of fluorescent drugs;
    an arithmetic processing section comprising at least a first hardware processor that is configured to acquire, based on the information stored in the memory, fluorescent drug information including:
        information concerning a target region of a subject to which a desired fluorescent drug is administered,
        information concerning a method of administering the desired fluorescent drug to the target region,
        information concerning start time of administration of the desired fluorescent drug, and
        information concerning diagnosis start time corresponding to the desired fluorescent drug;
    an image sensor that is configured to pick up an image of an object in the subject; and
    a position information acquiring section comprising at least a second hardware processor that is configured to acquire position information of the image sensor in the subject;
    wherein the arithmetic processing section is further configured to perform, based on the fluorescent drug information, determination concerning whether a current time reaches the diagnosis start time and to perform, based on the position information acquired by the position information acquiring section, determination concerning whether the image sensor reaches a periphery of the target region; and
    a light source control section comprising at least the first hardware processor that performs control to stop irradiation of excitation light for exciting the desired fluorescent drug, at least from the start time of the administration of the desired fluorescent drug to the diagnosis start time, and to start the irradiation of the excitation light when it is determined that the current time is at or after the diagnosis start time and the image sensor reaches the periphery of the target region.

2. The medical apparatus according to claim 1, wherein, when it is determined based on the determination result of the arithmetic processing section that the image pickup section passes the periphery of the target region, the light source control section performs control to cause a light source, which is configured to emit the excitation light and the white color light simultaneously or individually, to irradiate only the white color light.

3. The medical apparatus according to claim 1, wherein, when the image sensor does not reach a periphery of the target region, the image sensor is guided to the target region based on operation from an outside of the medical apparatus.

* * * * *